United States Patent [19]

Golub

[11] Patent Number: 4,799,888
[45] Date of Patent: Jan. 24, 1989

[54] DENTAL PROCESS WITH TREATED FABRIC

[76] Inventor: Jeff E. Golub, 128 E. 71st St., New York, N.Y. 10021

[21] Appl. No.: 927,504

[22] Filed: Nov. 6, 1986

Related U.S. Application Data

[63] Continuation-in-part of Ser. No. 878,640, Jun. 26, 1986, Pat. No. 4,728,291.

[51] Int. Cl.⁴ ............................................. A61C 5/00
[52] U.S. Cl. ............................ 433/215; 433/202.1; 433/223
[58] Field of Search .................... 433/223, 222.1, 219, 433/218, 217.1, 215, 202; 264/16, 19, 20

[56] References Cited

U.S. PATENT DOCUMENTS

| | | | |
|---|---|---|---|
| 269,249 | 7/1943 | Weikel | 433/202.1 |
| 2,793,436 | 5/1957 | Gotlib | 264/20 |
| 3,974,567 | 8/1976 | Ridgeway | 433/217.1 |
| 4,302,376 | 11/1981 | Walkowiak et al. | 106/35 |
| 4,388,069 | 6/1983 | Orlowski | 106/35 |
| 4,392,829 | 7/1983 | Tanaka | 433/222.1 |
| 4,433,960 | 2/1984 | Garito et al. | 433/215 |

Primary Examiner—Gene Mancene
Assistant Examiner—Adriene J. Lepiane
Attorney, Agent, or Firm—James P. Malone

[57] ABSTRACT

The process of reshaping a tooth comprising the steps of: applying Silane to a fabric bonding, applying the fabric to the tooth, bonding the fabric to the tooth, sculpting the bonded material, polishing and finishing the bonded material, wherein the fabric or cloth is silk or nylon, or other cloth.

5 Claims, 2 Drawing Sheets

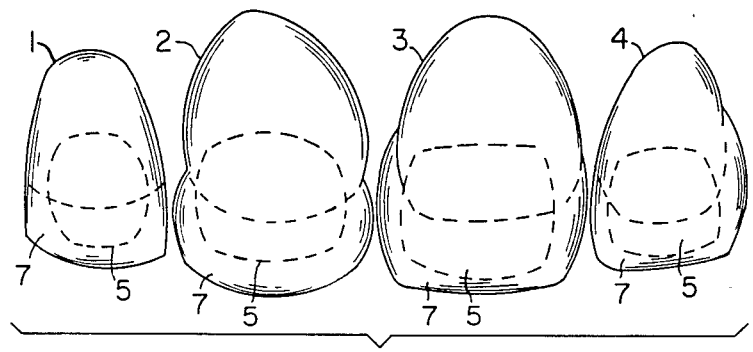
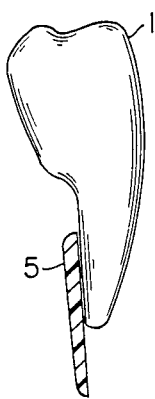
FIG. 5A
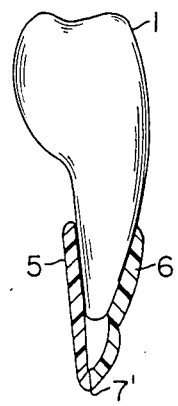
FIG. 5B
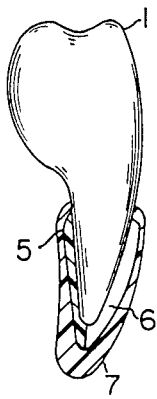
FIG. 5C

DENTAL PROCESS WITH TREATED FABRIC

This Application is a continuation-in-part of my prior application, Ser. No. 878,640 now U.S. Pat. No. 4,728,291, filed June 26, 1986, for "CLOTH WRAP DENTAL PROCESS".

TECHNICAL FIELD

This invention relates to a process of enhancing the external fixation of bonding resin for reshaping teeth, using Silane. Silane is a coating for fillers in composite fillings, and is also used as a coupling agent. It is manufactured by Union Carbide among others.

BACKGROUND AND PRIOR ART

Composite bonding resins can fracture. Unhappily, sometimes it is yesterday's bonding. But some bonding resins placed in the mouth 7, 10 or 14 years ago, though not always color stable, are still intact. This mystery has traditionally been answered by focussing on case selection; the resins have fared far better in low-stress areas. Resins placed in areas which overstress their tensile abilities will fail. Those of us who style smiles and are continually attempting to lengthen, widen and rotate teeth with composite materials have faced artistic and technical limitations. Cantilevering composites has been an anathema. Since these filled esins have no continuous internal matrices, they absorb stress almost entirely at the points of impact. Hence the more your composite resin hangs off the side of the tooth, the more the practitioner is out on a limb. If the patient is additionally a bruxer, the restoration will fail.

Buonocare, Jordan, Gwinnett, Pollack and others have described the properties and limitations of microfills, macrofills and hybrid bis-GMA resins. Clinicians have devices techniques to minimize the fracture of cantilevered composite resin; including, (1) over-relieving interferences in protrusive and lateral excursions, (2) rounding sharp line angles of the enamel structure, (3) utilizing as much enamel surface as possible for adhesion, (4) roughening the tooth surface with abrasive diamond stones before etching (Goldstein, Black), (5) insuring that the etchant and bonding adhesive wrap into the interproximal areas (Hendell), (6) using microfills for the majority of the buildup and microfills only for the final outer surface. Still, bonding has had its limitations. Teeth which have needed to be lengthened or widened considerably, such as openbite cases or malformed, retruded or malposed teeth (and of course missing teeth) have always required conventional crowns and conventioal bridges. Even Maryland Bridges have necessitated some form of metallic frame, and therefore, laboratory intervention.

THE INVENTION

My prior above mentioned application provides a new and different process for enhancing the external fixation of bonding resin. This application has developed a new procedure, the Dental Cloth Wrap With Silane. Much like a manicurist's nail extension, pieces of cloth are applied to the tooth, creating a matrix for additional bonding resin. Applicant has experimented with cotton, nylon, dacron and other synthetics; silk and nylon seem to work best. Silk, a proteinacious substance, has more little barbs than synthetic fibers for grabbing the resin. It is less rigid and therefore, more workable than cotton. As long cloth fibers are internalized with the ultimate composite resin, any fiber will probably be better than none. Applicant prefers either China Silk or the twenty gauge silk used by silk screeneres. The most useful colors are ivory, beige and white. This Application provides the addition of soaking or otherwise applying Silane. This is a conventional solution which greatly improves the bonding of the cloth to the teeth.

Silane is a chemical having one or more of the following forms vinyltriethoxy silane, vinyltrichloro silane, (gamma) g - amnio-propyltriethoxy silane, (gamma) g - methacryloxypropyln silane.

OBJECTS OF THE INVENTION

A principle object of the invention is to provide a new and improved process for enhancing the external fixation of bonding resin.

Another object of the invention is to provide a new and improved process for enhancing the external fixation of bonding resin, in the process of reshaping a tooth comprising the steps of: applying Silane to a fabric, applying the fabric to the tooth, bonding the fabric to the tooth, sculpturing the bonded material, polishing and finishing the bonded material for cosmetic and utilitarian purposes.

Another object of the invention is to provide a new and improved Dental Process, the process of reshaping a tooth comprising the steps of applying Silane to a fabric, applying the fabric to the tooth, bonding the fabric to the tooth, sculpturing the bonded material and polishing and finishing the bonded material.

A study model of the waxed mock-up is optional. The cloth will extend to within ½ mm. of the final bonded length.

BRIEF DESCRIPTION OF THE FIGURES:

These and other objects of the invention are apparent by the following specification and figures of which:

FIG. 4 is a front view of fabric-resin matric totally enveloped in bonding resin.

FIGS. 5A–5C show side views, partly in section of a tooth illustrating the process of the invention.

THE PROCESS IF AS FOLLOWS

Figure 1:
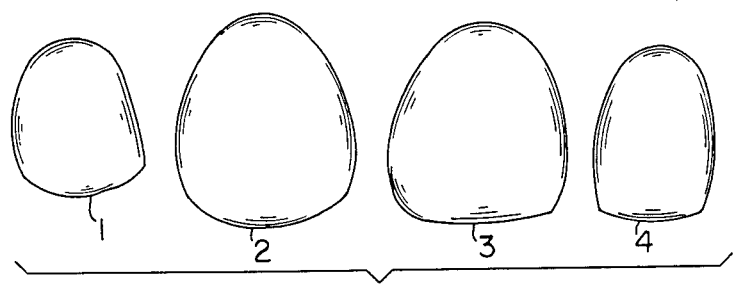
FIG. 1 is a front view of teeth to be enhanced by the present process.

1. After selecting an appropriate case, use soft orthodontic wax to approximate and mock-up the final restorations. A study model of the waxed mock-up is optional. The cloth will extend to within ½ mm. of the final bonded length.

2. Pumice the teeth, etch them on all surfaces, then use standard lavage and drying techniques.

3. Cut the cloth in ½ inch lengths measured as wide as the proximal incisal corners (less about ½ mm. from each edge). cut two for each tooth and hold aside. Apply Silane to the cloth, for instance, by soaking. Affix the cloth about half way up the tooth even for a 1 or 2 mm. extension. For bruxers, even the tiniest extension requires a cloth wrap. The fabric ribbons can actually be any length. The incisal excess will be cut later.

4. Apply the light-cured bonding liquid to the enamel surface and cure.

5. Mix a non-light cured luting agent. The cloth fibers are opaque. Chemically cured Concise, Comspan, Microjoin and Super C, all commercially available, have all been used with good results.

6. Place a cellophane strip loosely adjacent to the linqual surface wrapping labially through the two interproximals. Place the auto-cured adhesive paste on the lingual enamel and onto the sides. Wet the cloth strip thoroughly with paste. Compress the parts together with the cloth strip insuring that the extended silk is following the imaginary inclined plane of the ligual surface of the tooth. Remove any paste adhesive which spills onto the labial surface.

7. Optionally, place a bonding resin, preferably a macro type, at the incisal edge and slightly onto the labial surface to fill in the space.

8. Now apply a new mix of adhesive paste on the labial enamal and on a second piece of cloth. Compress again with a clear plastic strip against the hardened lingual cloth-resin complex.

9. Once set, reduce the fabric-resin structure with a dry medium diamond stone to within ½ millimeter of the ultimate bonded length and width. Check the occlusion.

10. Roughen any fabric-resin material which appears shiny and add light cured bonding adhesive to the silk structure and to the remaining enamel surface and cure it.

11. Add the composite resin, choosing a macrofill for the lingual surface for strength and a microfill for a labial surface for polish and luster.

12. Sculpt and finish as you would normally. The outer bending composite resin should envelope the cloth entirely and should be firmly attached to the labial, lingual and proximal enamel surfaces, as well as to the cloth-resin complex.

13. Polish and finish.

The present invention has been successfully tested. It is essential for bruxers, for extending short teeth in open bite cases, for closing extra-large diastemas, especially in lower teeth where the proximal stress is higher, for periodontal splinting, for Manhattan bridges and for teeth in crossbite.

Advantages of Silk to Wrap Teeth
1. Silk cloth has exceptional tensile properties.
2. Silk in combination with a macro resin produces a complex of unusual strength and durability.
3. Silk, a natural substance, is generally non-allergenic.
4. Silk can be fabricated in many colors.
5. Silk does not exercise undue water absorption properties.
6. Silk cloth has tiny microscopic barbs for grabbing the bonded resin.

The Present Dental Cloth Wrap Technique Can Be Used To
1. Widen teeth in preparation for bonding resin or laminates.
2. Lengthen teeth in preparation for bonding resin or laminates.
3. Reinforce weak teeth in preparation for bonding resin or laminates.
4. Rotate teeth in preparation for bonding resin or laminates.
5. Change teeth in crossbite in preparation for bonding resin or laminates.
6. Replace teeth in preparation for bonding resin or laminates.
7. Opaque teeth in preparation for bondng resin or laminates.
8. Splint loose teeth.
9. Reinforce temporary crowns and bridges.
10. Reinforce composite crowns.
11. Enable Manhattan composite bridges.

More specifically, FIG. 1 shows a set of teeth 1, 2, 3, 4, which are short and to be lengthened by the present process.

Figure 2:
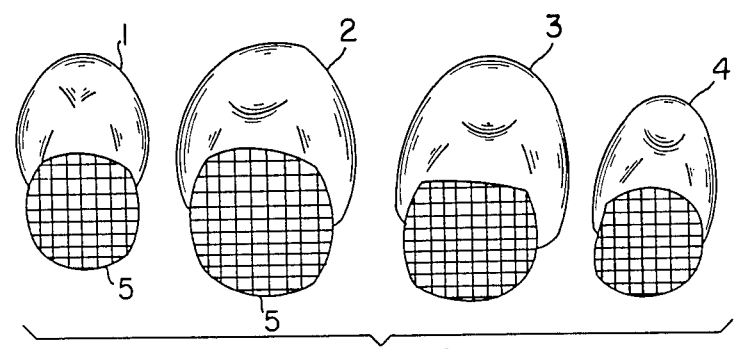
FIG. 2 shows a front view of fabric-resin complex placed on the lingual surfaces of the teeth.

FIG. 2, shows a fabric-resin complex 5, placed on the lingual surfaces of the teeth, 1 to 4. The fabric has been soaked in Silane.

Figure 3:
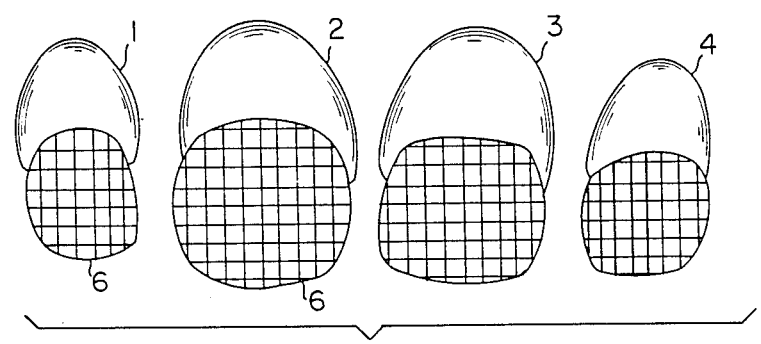
FIG. 3 is a front view of fabric-resin complex placed on the labial surfaces of the teeth.

FIG. 3 shows a fabric-resin complex 6, placed on the labial surface of the teeth 1 to 4.

FIG. 4 shows the fabric-resin complex, 5 or 6, enveloped in bonding resin 7.

FIG. 5A shows a side view of the fabric-resin complex 5 placed on the lingual surface.

FIG. 5B shows the fabric-resin complexes 5 and 6, mounted on the lingual and labial surfaces. FIG. 5B also shows the complexes 5 and 6 being joined together at point 7, for the purpose of lengthening the tooth 1.

FIG. 5C shows the fabric-resin matrix 5, 6, totally encased in bonding resin 7.

REFERENCES

Black, J. B.: Esthetic restoration of tetracycline stained teeth, J.A.D.A., 1982, 104: 846–852

Buonocore, M. G.: Retrospections on bonding, Dent. Clinics of N. Amer., Saunders, 1981 25 (2): 243

Buonocore, M. G.: A simple method of increasing the adhesion of acrylic filling materials to enamel surfaces, J. Dent. Res., 1955

Bowen, R. L.: Dental filling material comprising vinyl silane treated fused 1962 etc, 1962, U.S. Pat. No. 3,006,112

Boyer, D. B. et al: Build-up and repair of light-cured composites: bond strength, J. Den. Res, 1984, 63 (10): 1241–1244

Chan, K. G. and Boyer, D. B.: Repair of conventional and microfilled composite resins, J. Prosth. Dent, 1983, 50 (3): 345–50

Golub, J. E.: The role of the cosmetic dentist, New York State Dental Journal, 1985, (483–485)

Gwinnett, A. J.: Acid etching for composite resins, Dent. Clinics of N. Amer., 1981, 25 (2): 275

Gwinnett, A. J.: Personal communication

Hendell, D.: Lecture First Dist. Dent Soc. Continuing Education Program 1985, 1986

Jordan et al: Esthetic Composite Bonding

Pollack, B. F.: Personal communication

It is claimed:

1. The process of reshaping a tooth comprising the steps of:
   Applying Silane selected from the group consisting of vinyltriethoxy silane, vinyltrichloro sialne, (gamma) g - amniopropyltriethoxy silane, (gamma) g - methacryloxy propyln silane, to a cloth,
   applying the cloth to the tooth, bonding the cloth to the tooth, sculpturing the bonded material, polishing and finishing the bonded material.

2. The process of applying the bonded material as in claim 1 wherein the cloth is selected from the group consisting of silk and nylon.

3. The process for reshaping teeth as follows:
   (a) apply soft orthodontic wax to approximate and mock-up the final restorations, (b) pumice the teeth, etch them on all surfaces and then use standard lavage and drying techniques, (c) cut cloth in ½ inch lengths measured as wide as the proximal incisal corners, less about ½ mm, from each edge, cut two for each tooth and hold aside, (d) apply Silane-selected from the group consisting of vinyltriethoxy silane, vinyltrichloro silane, (gamma) g-amniopropyltriethoxy silane, (gamma) g-methacryloxy proplyn silane, to the cloth, (e) affix the cloth about half way up the tooth even for a 1 or 2 mm. extension, for bruxers, even the tiniest requires a cloth wrap, so that the cloth will extend to within ½ mm. of the final bonded length, (f) apply light-cured bonding liquid to the enamel surface and cure, (g) apply a non-light cured luting agent, (h) place a cellophane strip loosely adjacent to the lingual surface wrapping labially through the two interproximals, place autocured adhesive paste on the lingual surface of the enamel and onto the sides, wet the cloth thoroughly with the paste, compress the parts together with the cellophane strip insuring that the extended cloth is following the imaginary inclined plane of the lingual surface of the tooth, remove any paste adhesive which spills onto the labial surface, (i) apply a new mix or adhesive paste on the labial surface of the enamel and on a second piece of cloth, compress again with a clear plastic strip, (j) once set, reduce the cloth structure with a dry medium diamond stone to within ½ millimeter of the ultimate bonded length and width, check the occlusion, (k) roughen any material which appears shiny and add light cured bonding adhesive to the cloth structure and to the remaining enamel surface and cure it, (l) add composite resin, choosing a microfill for the lingual surface for strength and a microfill for the labial surface for polish and luster, (m) sculpt and finish normally the outer bonding composite resin, should envelope the cloth entirely and should be firmly attached to the labial, lingual and proximal enamel surfaces, as well as to the cloth-resin complex, (n) polish and finish.

4. The process as in claim 3 adding the following step after step "h"- h (1) place a bonding resin, preferably a micro type at the incisal edge and slightly onto the labial surface to fill in the space.

5. The process as in claim 3, wherein the cloth is selected from the group consisting of silk and nylon.

* * * * *